United States Patent [19]

Watson et al.

[11] Patent Number: 5,738,666

[45] Date of Patent: Apr. 14, 1998

[54] SLIT TIP VENTRICULAR CATHETER AND METHOD OF MANUFACTURING SAME

[75] Inventors: David A. Watson, Goleta; Lori Cone Speckman, Ventura, both of Calif.

[73] Assignee: Medtronic, Inc., Minneapolis, Minn.

[21] Appl. No.: 678,669

[22] Filed: Jul. 10, 1996

Related U.S. Application Data

[62] Division of Ser. No. 405,352, Mar. 16, 1995, abandoned.

[51] Int. Cl.$^6$ ...................................................... A61M 5/00
[52] U.S. Cl. ........................ 604/264; 604/247; 604/265
[58] Field of Search ................................ 604/264, 265, 604/268, 280, 167, 247; 128/344; 427/2.3; 29/825; 623/1

[56] References Cited

U.S. PATENT DOCUMENTS

| | | |
|---|---|---|
| 3,941,121 | 3/1976 | Olinger et al. . |
| 4,549,879 | 10/1985 | Groshong et al. ............... 604/247 |
| 4,736,733 | 4/1988 | Adair . |
| 4,771,777 | 9/1988 | Horzewski et al. ............... 128/344 |
| 4,986,814 | 1/1991 | Burney et al. . |
| 5,120,317 | 6/1992 | Luther . |
| 5,127,393 | 7/1992 | McFarlin et al. . |
| 5,131,380 | 7/1992 | Heller et al. . |
| 5,159,920 | 11/1992 | Condon et al. . |
| 5,193,525 | 3/1993 | Silverstein et al. . |
| 5,195,541 | 3/1993 | Obenchain . |
| 5,201,743 | 4/1993 | Haber et al. . |
| 5,201,908 | 4/1993 | Jones . |
| 5,217,001 | 6/1993 | Nakao et al. . |
| 5,254,112 | 10/1993 | Sinofsky et al. . |
| 5,263,928 | 11/1993 | Trauthen et al. . |
| 5,292,305 | 3/1994 | Boudewijn et al. . |
| 5,312,327 | 5/1994 | Bales et al. . |
| 5,312,332 | 5/1994 | Bales et al. . |
| 5,314,406 | 5/1994 | Arias et al. . |
| 5,336,192 | 8/1994 | Palestrant . |
| 5,464,650 | 11/1995 | Berg et al. .......................... 427/2.3 |
| 5,473,812 | 12/1995 | Morris et al. ........................ 29/825 |
| 5,540,661 | 7/1996 | Tomisaka et al. ................. 604/265 |
| 5,607,463 | 3/1997 | Schwartz et al. ..................... 623/1 |

FOREIGN PATENT DOCUMENTS 3724978  2/1989  Germany .......................... 604/247

OTHER PUBLICATIONS

Neuro Navigational Neuroview™ Neuroendoscope product literature, Jul., 1993.
Biomedical Technology™ Information Service, vol. 21, No. 7, Apr. 15, 1994.

Primary Examiner—Michael Buiz
Assistant Examiner—Julian W. Woo
Attorney, Agent, or Firm—Kelly Bauersfeld Lowry & Kelley, LLP

[57] ABSTRACT

A partially disposable instrument for use in a medical procedure includes a rigid introducer assembly and a fiber-optic endoscope having a flexible shaft which may be removably inserted through the introducer assembly. The introducer assembly permits a fluid to be flushed therethrough and about the shaft such that the fluid exits through a terminal end of the introducer assembly. The instrument may be utilized in connection with a method for positioning a catheter within a body during a medical procedure, including the steps of placing the catheter over the introducer, inserting the shaft of the endoscope through the introducer, advancing the catheter, introducer and endoscope shaft into the body as a unit, positioning the catheter within the body utilizing the fiber-optic endoscope, and removing the endoscope shaft and the introducer from the body while leaving the catheter in place. The catheter includes a slit tip capable of opening to permit the terminal end of the introducer assembly to pass therethrough such that the diameter of the slit tip, when so configured, is not significantly greater than a nominal diameter of the catheter.

18 Claims, 3 Drawing Sheets

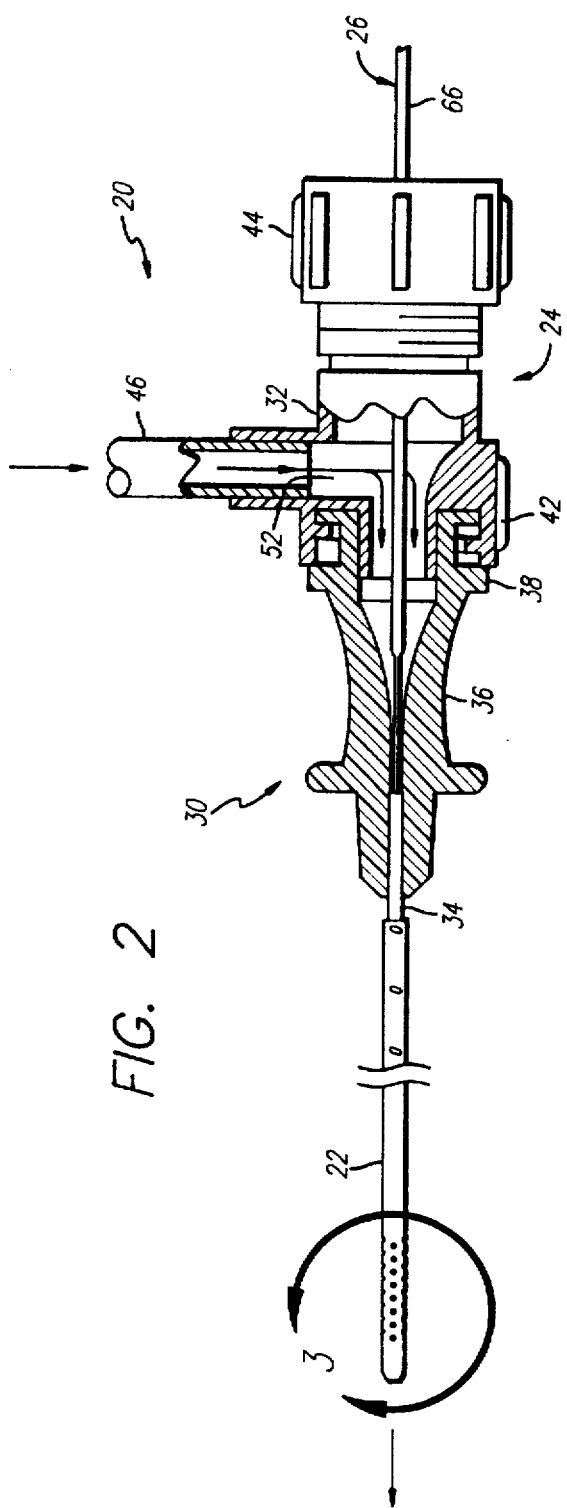
FIG. 2
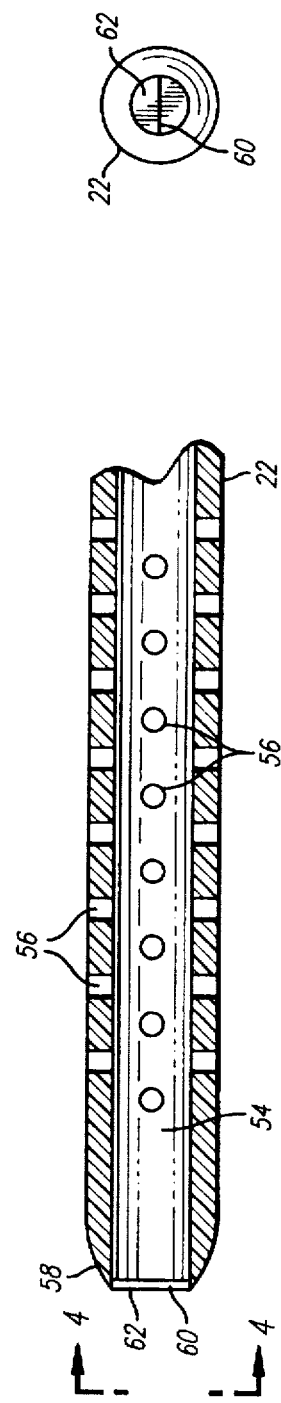
FIG. 3
FIG. 4

SLIT TIP VENTRICULAR CATHETER AND METHOD OF MANUFACTURING SAME

This is a division, of application Ser. No. 08/405,352, filed Mar. 16, 1995, now abandoned.

BACKGROUND OF THE INVENTION

This invention relates generally to medical instruments and surgical procedures. More specifically, the present invention relates to an imaging device utilized in the placement of ventricular catheters in the treatment of hydrocephalus.

Puncture of the lateral ventricle and placement of a flexible silastic catheter into the ventricular system is a very common procedure performed for a variety of indications including introduction of contrast or chemotherapy, measurement of intracranial pressure, the treatment of hydrocephalus, and collection of cerebrospinal fluid. Current medical procedure typically involves use of a rigid obturator or stylet situated within a flexible catheter, which are commonly introduced together through the brain into the cerebral ventricle. The tip of the catheter is caused to remain in the cerebral ventricle when the stylet is removed from the patient.

Complications which arise during placement of the catheter include injury to vascular structures such as the choroid plexus, injury to neurological structures, and improper location of the tip. These problems can result in an increased catheter malfunction rate requiring reinsertion.

A variety of endoscopes with working ports have been used to inspect and treat disorders of the cerebral ventricles. Such endoscopes are typically large compared to the internal diameters of current ventricular catheters and therefore, they have not been situated inside ventricular catheters. However, the advantages of using fiber-optic technology in connection with the placement of medical devices within a fluid-filled cavity in a body are obvious. In the treatment of hydrocephalus, such technology would permit the tip of the ventricular catheter to . be correctly positioned for maximum results.

An important consideration in the design and use of most medical instruments, which would be applicable to fiber-optic endoscopes utilized in the treatment of hydrocephalus, is that the instruments must be cleaned and sterilized between each use. However, currently available endoscopes contain passageways to permit flushing of the lens at the terminal end. These passageways characteristically have very small diameters and are very difficult to disinfect, thus creating the potential of passing disease-bearing organisms between patients.

It has been suggested that disposable endoscopes be utilized, but it is believed that such would result in an abnormally high cost of use which is not justified. Another alternative is the use of a sanitary disposable sheath for medical instruments shown, for example, in U.S. Pat. No. 5,201,908.

Accordingly, there has been a need for a novel imaging assembly which advantageously utilizes the latest developments in fiber-optic imaging techniques to permit a surgeon to accurately position, for example, the tip of a ventricular catheter within a patient without increasing the risk of infection. Such an endoscope and related structure should lend itself well for use with current surgical procedures and address the sterility issues noted above. In this regard, it is preferred that the more expensive parts of the endoscope, including any fiber-optic components, not contain working channels to facilitate sterilization for reuse, while less expensive components, such as a stylet or introducer containing the working or flushing channels, should be disposable. The present invention fulfills these needs and provides other related advantages.

SUMMARY OF THE INVENTION

The present invention resides in devices and instruments utilized in medical procedures, namely a partially disposable instrument including a rigid introducer assembly, which is disposable, a reusable imaging assembly having a flexible shaft which may be removably inserted through the introducer assembly, and a ventricular catheter. The ventricular catheter includes a slit tip capable of opening to permit a terminal end of the introducer assembly to pass therethrough such that the diameter of the slit tip, when so configured, is not significantly greater than a nominal diameter of the catheter. The present invention also resides in a related method for positioning a catheter within the body, and a method for manufacturing the slit tip for the ventricular catheter.

The devices and related methods of the present invention permit a surgeon to accurately position, for example, a slit tip ventricular catheter within a brain ventricle in the treatment of hydrocephalus, in an efficient and cost effective manner. The imaging assembly contains fiber-optic bundles within the flexible shaft which is inserted through the rigid introducer assembly to position an end of the shaft adjacent to a terminal end of the introducer assembly. Means are provided for flushing a fluid through the introducer assembly and about the shaft such that the fluid exits through the terminal end of the introducer assembly.

In a preferred form of one aspect of the invention, the introducer assembly comprises a tubular cannula and a hub fixed to an end of the cannula. The fluid flushing means includes a Tuohy-Borst adapter with a side arm, and luer-lock means for coupling the Tuohy-Borst adapter to the introducer hub. The Tuohy-Borst adapter includes means for fixing the imaging assembly against movement relative to the introducer assembly. The side arm comprises a conduit in fluid communication with the introducer assembly through the Tuohy-Borst adapter, and means at an end of the fluid conduit opposite the adapter, for connection to a fluid source.

A method for positioning a catheter within a body during a medical procedure comprises the steps of, generally, placing the catheter over an introducer, and inserting an imaging assembly through the introducer. The catheter, introducer and imaging assembly are advanced into the body utilizing the imaging assembly to position the catheter as desired. The imaging assembly and the introducer are then removed from the body while leaving the catheter in place.

In accordance with one preferred method embodying the invention, the step of placing the catheter over the rigid introducer includes the step of extending a terminal end of the introducer through a tip of the catheter. The terminal end of the imaging assembly is then aligned with the terminal end of the introducer, and such aligned terminal ends are withdrawn into the catheter prior to advancing the catheter, introducer and imaging assembly into the body. In order to position the catheter within the body utilizing the imaging assembly, the aligned terminal imaging ends of the introducer and the assembly are re-extended through the tip of the catheter. In this regard, the imaging assembly typically comprises a fiber-optic endoscope which is utilized to visually determine the position of the tip of the catheter within the body.

During placement of the catheter within the body, fluid is flushed through the introducer and about the fiber-optic endoscope, as required, such that the fluid exits through the terminal end of the introducer. Additionally, a catheter is utilized which has a slit tip at its terminal end which is minimally opened as the introducer is passed therethrough such that the diameter at the slit tip, when so configured, is not significantly greater than a nominal diameter of the catheter.

In this regard, and with respect to another aspect of the present invention, the slit tip for the ventricular catheter is preferably manufactured by first grinding one end of the catheter into a bullet shape and then applying a tantalum/adhesive mixture to the ground end of the catheter. The ground end of the catheter is then coated with a dispersion, after which the ground end is permitted to dry. The tantalum/adhesive mixture on the ground end of the catheter is then cut to form the slit tip.

More specifically, the ventricular catheter comprises a cut section of silicone elastomer catheter tubing. After the end of the catheter has been ground into a bullet shape, it is cleaned with isopropyl alcohol. A mixture of equal parts by weight tantalum and room-temperature-vulcanizing silicone adhesive is prepared for application to the ground end of the catheter during the applying step. A 325 mesh-size tantalum is utilized in the mixture.

The tantalum/adhesive mixture is applied to the ground end of the catheter utilizing a syringe with a blunt needle adapter. Utilizing such an apparatus, a thin coat of the tantalum/adhesive mixture is applied to the ground catheter tip. The ground end of the catheter and the applied tantalum/adhesive mixture is allowed to air dry for a minimum of ten minutes. Any sink marks which develop in the tantalum/adhesive mixture are filled, and the tantalum/adhesive mixture is allowed to cure at room temperature.

A dispersion of heat-vulcanizing silicone elastomer in xylene is prepared, and then utilized to coat the ground end of the catheter. The coated tantalum/adhesive mixture is then cured in a heated oven. Finally, the cured tantalum/adhesive mixture is cut utilizing a single-edge razor blade having a width approximately that of the ventricular catheter inner diameter.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 2 is an enlarged elevational and partially sectional view of the disposable introducer assembly illustrated in FIG. 1, wherein the ventricular catheter is placed over a cannula, and further illustrating insertion of shaft of the fiber-optic endoscope through the introducer;

FIG. 3 is an enlarged, fragmented sectional view taken generally about the area indicated by the arrow 3 in FIG. 2, illustrating the slit tip of the ventricular catheter prior to insertion of the introducer assembly;

FIG. 4 is an elevational view taken generally along the line 4—4 of FIG. 3;

DETAILED DESCRIPTION OF THE PREFERRED EMBODIMENT

Figure 1:
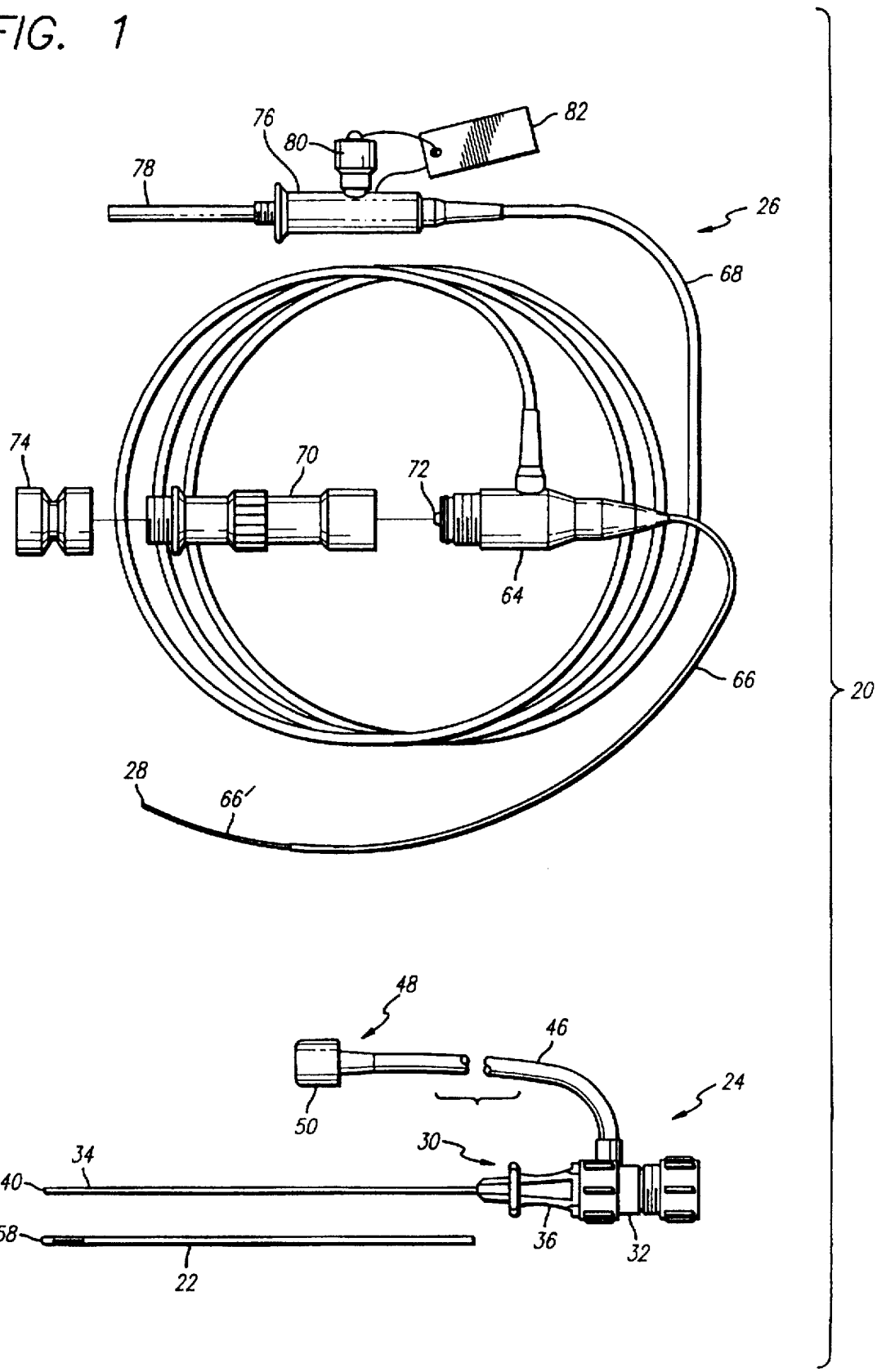
FIG. 1 is a perspective view of the various components comprising the partially-disposable instrument for use in a medical procedure embodying the invention, including a fiber-optic endoscope imaging assembly, a disposable introducer assembly, and a ventricular catheter having a slit tip.

As shown in the drawings for purposes of illustration, the present invention is concerned with a partially disposable instrument, designated in the accompanying drawings by the reference number 20, useful in positioning a ventricular catheter 22 within a body during a medical procedure. The instrument 20 includes an introducer assembly 24 over which the ventricular catheter 22 is placed, and an imaging assembly comprising a fiber-optic endoscope 26. A flexible shaft of the fiber-optic endoscope 26 may be placed through the introducer assembly 24 to position a terminal end 28 of the flexible shaft adjacent to the tip of the ventricular catheter 22.

In accordance with the present invention, and as shown best in FIGS. 1 and 2, the introducer assembly 24 comprises a disposable introducer 30 connected to a Tuohy-Borst adapter 32 by means of a luer-lock. The introducer 30 includes a rigid tubular cannula 34 which supports a hub 36 that includes a female luer-lock 38. An interior passageway is defined through the introducer 30 from the hub 36 to a terminal end 40 of the introducer 30.

The Tuohy-Borst adapter 32 is of standard construction and includes a male luer-lock 42 and a cap 44. A side arm 46 extends radially away from the adapter 32, which terminates at a female luer-lock 48 closed by a suitable closure 50. The side arm 46 provides a fluid conduit from the female luer-lock 48 to an interior portion 52 of the introducer assembly 24 through the Tuohy-Borst adapter 32. The female luer-lock 48 is adapted for connection to a fluid source (not shown) through which a fluid, such as a sterile saline solution, may be injected in order to clear the terminal end 40 of the introducer 30 of obstructions.

Figure 7:
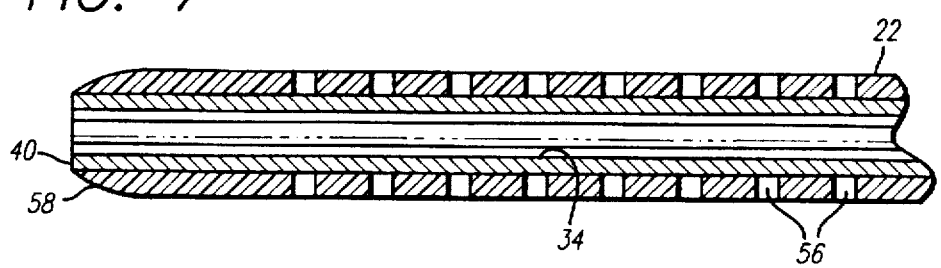
FIG. 7 is a fragmented sectional view similar to FIGS. 3, 5 and 6, illustrating alignment of the ends of the fiber-optic endoscope and the introducer assembly with the tip of the ventricular catheter.
Figure 8:
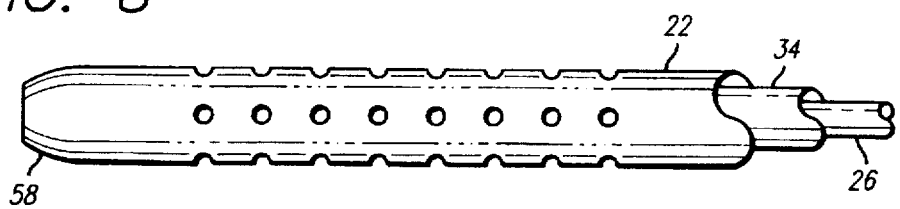
FIG. 8 is a partially fragmented elevational view of the assembly illustrated in FIG. 7, showing configuration of the ventricular catheter with the slit tip fully opened by the introducer assembly.
Figure 9:
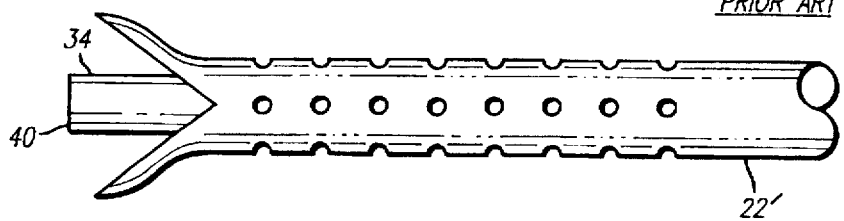
FIG. 9 is a partially fragmented elevational view similar to that shown in FIG. 8, illustrating the manner in which prior art slit tip ventricular catheters open to permit fiber-optic endoscopes to extend therethrough.

The ventricular catheter 22 is preferably manufactured of a silicone elastomer material and includes a lumen 54 which has a greater diameter than the outer diameter of the cannula 34. A plurality of fluid flow apertures 56 are provided through the wall of the catheter 22 adjacent to its tip 58. The tip 58 itself includes a slit 60 which is capable of opening to permit the terminal end 40 of the introducer 30 to pass therethrough such that the diameter of the slit tip 60, when so configured, is not significantly greater than a nominal diameter of the catheter 22 (See FIGS. 7 and 8). To achieve this, the tip 58 is so configured that the length of the slit 60 is less than the nominal outside diameter of the catheter 22. By way of comparison, FIG. 9 illustrates a prior art catheter 22' having a slit tip which causes the tip of the catheter to open well beyond the nominal diameter of the catheter itself. (See FIGS. 3 and 4).

In order to manufacture the ventricular catheter 22 so as to include the novel slit tip 60, first a segment of silicone elastomer catheter tubing is cut to length. Using a grinding wheel, the tip 58 is ground into the bullet shape shown in FIGS. 3, 4 and 8. Following the grinding operation, the tip 58 is cleaned with isopropyl alcohol.

A mixture of equal parts by weight 325 mesh size tantalum and room-temperature-vulcanizing silicone adhesive is then prepared, and then a syringe with a blunt needle adapter (not shown) is utilized to apply a thin coat of the tantalum/adhesive mixture to the ground catheter tip 58. This tantalum/adhesive mixture fills and occludes the terminal end of the lumen 54 of the ventricular catheter 22. The tip 58 is then allowed to air dry for a minimum of ten minutes. Any "sink" in the plug formed by the applied tantalum/adhesive mixture 62 is filled, and the mixture is permitted to cure at room temperature for a minimum of six hours.

Next, a dispersion of heat-vulcanizing silicone elastomer in xylene is prepared. The catheter tip 58 is then dipped in the silicone dispersion, and the tip 58 is then allowed to air dry for five to ten minutes. The tip 58 after having been dipped in the dispersion has the silicone elastomer cured in a heated oven for thirty minutes at 310° F. Use of the silicone elastomer dispersion improves the aesthetics and smoothness of the catheter tip 58 in the ground area.

Finally, a single-edge razor blade is prepared with a width approximately that of the lumen 54 of the ventricular catheter 22. This blade is utilized to slit the tantalum/adhesive mixture 62 in the tip 58 of the ventricular catheter to create the slit tip 60.

The fiber-optic endoscope 26 is of such construction and operates in a manner known to those skilled in the art. The endoscope 26 includes a housing 64 from which extends a fiber-optic shaft 66 and a light cable 68. An optics module 70 attaches to the housing 64 over the end of an imaging bundle 72, and an eyepiece adapter 74 attaches to the optics module 70 opposite the housing 64, all in a known manner.

The light cable 68, opposite the housing 64, is attached to a vent housing 76 which, in turn, supports a light cable post 78. The light cable post 78 can take many different forms in order to adapt to various light sources. The vent housing is provided a vent cap 80 and an instruction tab 82, as shown.

The diameter of a portion 66' of the fiber-optic shaft 66 adjacent to the terminal end 28 thereof is less than the interior diameter of the cannula 34. It is desirable to have space between the exterior surface of the reduced diameter portion 66' of the fiber-optic shaft 66 and the interior of the cannula 34 in order to permit fluid to be flushed through the introducer assembly 24 to exit through the terminal end 40 of the cannula 34.

To use the imaging assembly of the present invention to position the catheter 22 within a brain ventricle, the catheter 22 is first placed over the cannula 34 of the introducer 30 so that the terminal end 40 of the introducer assembly 24 extends through the slit tip 60 of the catheter.

Figure 5:
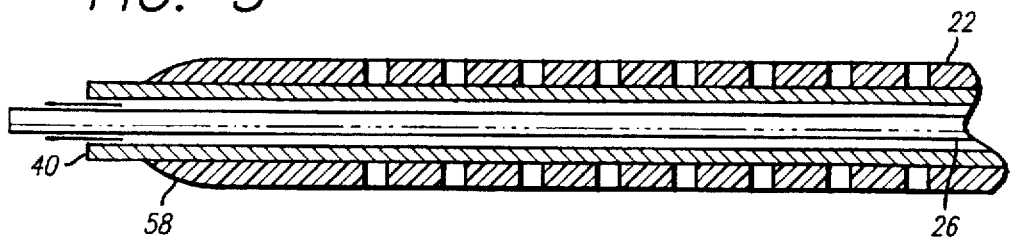
FIG. 5 is a fragmented sectional view similar to that shown in FIG. 3, illustrating the step of extending a terminal end of the introducer assembly through the slit tip, and also extending the terminal end of the endoscope shaft beyond the terminal end of the introducer assembly.
Figure 6:
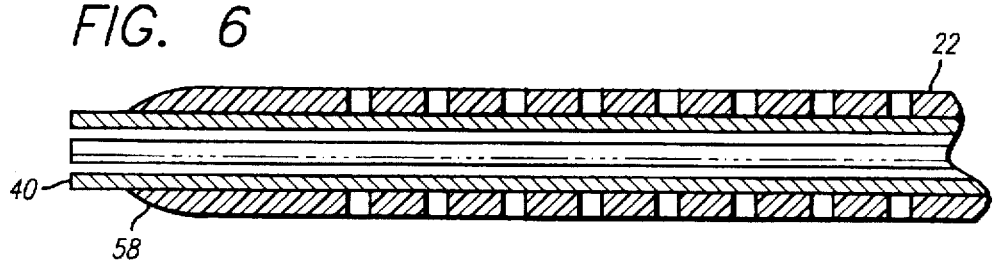
FIG. 6 is a fragmented sectional view similar to that shown in FIGS. 3 and 5, illustrating the step of pulling the shaft of the endoscope back into the introducer assembly until the ends are even with one another.

The terminal end 28 of the fiber-optic cable is inserted through the cap 44 of the Tuohy-Borst adapter 32 and through the introducer 30 so that the terminal end 28 thereof extends past the terminal end 40 of the introducer 30 (see FIG. 5). It is preferred that the terminal end 28 of the fiber-optic cable be aligned with the end 40 of the introducer 30 (FIGS. 6–8), and when so positioned the shaft 66 of the fiber-optic endoscope 26 may be locked into place by turning the cap 44. The aligned tips of the endoscope and the introducer 30 will be retracted into the catheter 22 while the assembly is advanced into the body, and extended through the slit tip 60 after reaching the ventricle. The fiber-optic endoscope 26 will generate a direct image of the interior of the ventricle and provide for correct placement of the tip 58 of the catheter 22.

Since the fiber-optic endoscope 26 provides a direct image of the ventricle, occasionally the terminal end 28 of the endoscope 26 may be covered with a material that would obscure the surgeon's vision of the ventricle itself. In this case, the closure 50 may be removed from the luer-lock 48 of the side arm 46, and a sterile saline solution may be injected therethrough to flush the end 28 of the endoscope 26 to permit better vision. The portion 66' of the fiber-optic shaft 66 extending through the cannula 34 of the introducer 30 is dimensioned-so as to permit fluid to be flushed through the introducer and about the shaft such that the fluid exits the introducer 30 through its terminal end 40.

Once the tip 58 of the catheter 22 is properly placed, the fiber-optic endoscope 26 and the introducer 30 are removed from the catheter 22, leaving the catheter in place. The introducer assembly 24 may then be discarded, whereas the more expensive fiber-optic endoscope 26 may be easily cleaned and sterilized in preparation for use with another patient.

From the foregoing it is to be appreciated that the partially disposable instrument 20 provides advantages not heretofore known in the treatment of diseases such as hydrocephalus, wherein precise catheter placement within the body is required. Direct visualization of the location of the tip 58 of the catheter 22 allows accurate placement within the ventricle and may preclude the need for X-ray confirmation of placement of the catheter tip.

Although a particular embodiment of the invention has been described in detail for purposes of illustration, various modifications may be made without departing from the spirit and scope of the invention. Accordingly, the invention is not to be limited, except as by the appended claims.

We claim:

1. A tubular catheter with a wall having a nominal outside diameter for placement within a body, comprising:
   a terminal end having an outer diameter the same as or less than the nominal outside diameter;
   a plurality of fluid flow apertures in the wall adjacent to the terminal end;
   an elastomeric closure for the terminal end; and
   at least one slit through the closure such that the length of the slit is less than the nominal outside diameter.

2. The catheter of claim 1, wherein the elastomeric closure comprises a mixture of equal parts by weight tantalum and room-temperature-vulcanizing silicone adhesive.

3. The catheter of claim 2, wherein the terminal end is ground into a bullet shape, and wherein the slit extends the diameter of the elastomeric closure.

4. The catheter of claim 3, wherein the catheter comprises a cut section of silicone elastomer catheter tubing.

5. The catheter of claim 4, wherein the tantalum comprises 325 mesh size tantalum.

6. The catheter of claim 3, including a dispersion applied over the terminal end of the catheter and an exposed surface of the elastomeric closure.

7. The catheter of claim 6, wherein the dispersion comprises a heat-vulcanizing silicone elastomer in xylene.

8. A method for manufacturing a slit tip for a ventricular catheter, comprising the steps of:

grinding one end of the catheter into a bullet shape;

applying a tantalum/adhesive mixture to the ground end of the catheter;

coating the ground end of the catheter with a dispersion;

drying the ground end of the catheter; and cutting the tantalum/adhesive mixture on the ground end of the catheter to form the slit tip.

9. The method of claim 8, including the step of cleaning the ground end of the catheter with isopropyl alcohol prior to the step of applying the tantalum/adhesive mixture thereto.

10. The method of claim 8, including the step of preparing a mixture of equal parts by weight tantalum and room-temperature-vulcanizing silicone adhesive for application to the ground end of the catheter during the applying step.

11. The method of claim 10, including the step of utilizing 325 mesh size tantalum in the mixture.

12. The method of claim 8, wherein the step of applying the tantalum/adhesive mixture to the ground end of the catheter includes the step of utilizing a syringe with a blunt needle adapter to apply a thin coat of the tantalum/adhesive mixture to the ground catheter tip.

13. The method of claim 8, including the step of allowing the ground end of the catheter and the applied tantalum/adhesive mixture to air dry following the step of applying the tantalum/adhesive mixture to the ground end of the catheter.

14. The method of claim 13, wherein the drying time is a minimum of ten minutes.

15. The method of claim 14, including the steps of filling in any sink mark which develops in the tantalum/adhesive mixture, and allowing the tantalum/adhesive mixture to cure at room temperature.

16. The method of claim 8, including the step of preparing a dispersion of heat-vulcanizing silicone elastomer in xylene to be used during the step of coating the ground end of the catheter with the dispersion.

17. The method of claim 8, including the step of curing the coated tantalum/adhesive mixture applied to the ground end of the catheter in a heated oven.

18. The method of claim 8, wherein the step of cutting the tantalum/adhesive mixture includes the step of utilizing a single-edge razor blade having a width approximately that of the ventricular catheter inner diameter.

* * * * *